United States Patent
Anikanov et al.

(10) Patent No.: US 10,582,855 B2
(45) Date of Patent: *Mar. 10, 2020

(54) COMPACT SPECTROMETER SYSTEM FOR NON-INVASIVE MEASUREMENT OF ABSORPTION AND TRANSMISSION SPECTRA IN BIOLOGICAL TISSUE SAMPLES

(71) Applicant: SAMSUNG ELECTRONICS CO., LTD., Suwon-si (KR)

(72) Inventors: Alexey Grigor'evich Anikanov, Moscow (RU); Sergey Vasil'evich Afanasyev, Moscow (RU); Vladislav Vladimirovich Druzhin, Moscow (RU); Alexander Victorovich Morozov, Moscow (RU)

(73) Assignee: SAMSUNG ELECTRONICS CO., LTD., Suwon-si (KR)

(*) Notice: Subject to any disclaimer, the term of this patent is extended or adjusted under 35 U.S.C. 154(b) by 0 days.

This patent is subject to a terminal disclaimer.

(21) Appl. No.: 16/363,504

(22) Filed: Mar. 25, 2019

(65) Prior Publication Data
US 2019/0216322 A1    Jul. 18, 2019

Related U.S. Application Data

(63) Continuation of application No. 15/993,887, filed on May 31, 2018, now Pat. No. 10,258,236, which is a (Continued)

(30) Foreign Application Priority Data

Nov. 25, 2016  (RU) ................. 2016146355

(51) Int. Cl.
*G01J 3/00* (2006.01)
*A61B 5/00* (2006.01)
(Continued)

(52) U.S. Cl.
CPC .......... *A61B 5/0028* (2013.01); *A61B 5/0059* (2013.01); *A61B 5/0075* (2013.01);
(Continued)

(58) Field of Classification Search
CPC ...... G01J 3/02; G01J 3/28; G01J 3/42; G01N 21/31; G01N 21/552
(Continued)

(56) References Cited

U.S. PATENT DOCUMENTS 6,744,505 B1   6/2004   Wang et al.
6,747,742 B1   6/2004   Verma
(Continued)

FOREIGN PATENT DOCUMENTS

DE   10202050 A1   7/2003
JP   4536810 B2   9/2010
(Continued)

OTHER PUBLICATIONS

Communication dated Feb. 9, 2018, from the European Patent Office in counterpart European Application No. 17203454.8.
(Continued)

*Primary Examiner* — Md M Rahman
(74) *Attorney, Agent, or Firm* — Sughrue Mion, PLLC

(57) ABSTRACT

A spectrometer includes an illuminating section; a receiving section configured to detect radiation reflected from an object including an optically inhomogeneous scattering medium; a hardware section configured to obtain a solution of an inverse problem to reconstruct an absorption spectrum of the optically inhomogeneous scattering medium, wherein the illuminating section includes at least one light-emitting diode source, a radiation spectral curve of which is divided, by at least two spectral filters having different spectral transmission curves, into at least two spectral regions, to form an equivalent radiation spectrum from at least two
(Continued)

spectral sources, and wherein the hardware section applies the solution of the inverse problem based on information about a spectral content of the radiation of the illuminating section, a signal obtained in a form of a response from the optically inhomogeneous scattering medium, and a spectral sensitivity curve of the receiving section.

15 Claims, 9 Drawing Sheets

Related U.S. Application Data continuation of application No. 15/793,482, filed on Oct. 25, 2017, now Pat. No. 10,004,399.

(51) Int. Cl.
    *G01J 3/10*     (2006.01)
    *G01J 3/28*     (2006.01)
    *G01J 3/42*     (2006.01)
    *G01J 3/12*     (2006.01)

(52) U.S. Cl.
    CPC .............. *A61B 5/6801* (2013.01); *G01J 3/10* (2013.01); *G01J 3/28* (2013.01); *G01J 3/42* (2013.01); *G01J 2003/123* (2013.01); *G01J 2003/1213* (2013.01); *G01J 2003/1221* (2013.01); *G01J 2003/1282* (2013.01)

(58) Field of Classification Search
    USPC ........................................................ 356/300
    See application file for complete search history.

(56) References Cited

U.S. PATENT DOCUMENTS

| | | | |
|---|---|---|---|
| 7,034,935 B1 | 4/2006 | Kruzelecky | |
| 7,084,974 B1 | 8/2006 | Barwicz et al. | |
| 7,236,237 B2 | 6/2007 | Schmilovitch et al. | |
| 7,375,334 B2 | 5/2008 | Smith et al. | |
| 7,692,790 B2 | 4/2010 | Kerstan et al. | |
| 7,773,802 B2 | 8/2010 | Komiya et al. | |
| 7,889,919 B2 | 2/2011 | Komiya et al. | |
| 8,068,578 B2 | 11/2011 | Krauss | |
| 8,149,415 B2 | 4/2012 | Sanders et al. | |
| 8,711,362 B2 | 4/2014 | Funamoto | |
| 8,932,223 B2 | 1/2015 | Emelianov et al. | |
| 9,046,412 B2 | 6/2015 | Mortimer | |
| 9,234,839 B2 | 1/2016 | Hruska et al. | |
| 9,360,366 B1 | 6/2016 | Tran | |
| 9,360,415 B2 | 6/2016 | Liu et al. | |
| 9,395,244 B2 | 7/2016 | Kurokawa et al. | |
| 2004/0081621 A1 | 4/2004 | Arndt et al. | |
| 2005/0020892 A1 | 1/2005 | Acosta et al. | |
| 2005/0033127 A1 | 2/2005 | Ciurczak et al. | |
| 2005/0052649 A1 | 3/2005 | Tsujita | |
| 2007/0040997 A1* | 2/2007 | Yamauchi | G02B 27/46 353/97 |
| 2007/0092056 A1 | 4/2007 | Flohr et al. | |
| 2008/0108887 A1 | 5/2008 | Higgins | |
| 2009/0006052 A1* | 1/2009 | Zhou | G06T 15/50 703/5 |
| 2010/0056928 A1 | 3/2010 | Zuzak et al. | |
| 2013/0123639 A1 | 5/2013 | Ando | |
| 2014/0168636 A1 | 6/2014 | Funamoto | |
| 2014/0268136 A1* | 9/2014 | Pawluczyk | G01J 3/027 356/326 |
| 2014/0307249 A1 | 10/2014 | Peremans et al. | |

FOREIGN PATENT DOCUMENTS

| | | |
|---|---|---|
| KR | 10-2015-0110899 A | 10/2015 |
| WO | 2004/069164 A2 | 8/2004 |
| WO | 2010/082852 A1 | 7/2010 |

OTHER PUBLICATIONS

Georg Hennig et al., "Bandwidth-variable tunable optical filter unit for illumination and spectral imaging systems using thin-film optical band-pass filters", Review of Scientific Instruments, 84, 043113, (2013), (8 Pages Total).
Umpei Kurokawa et al., "Filter-Based Miniature Spectrometers: Spectrum Reconstruction Using Adaptive Regularization", IEEE Sensors Journal, vol. 11, No. 7, Jul. 2011, (8 Pages Total).
William K. Pratt et al., "Spectral estimation techniques for the spectral calibration of a color image scanner", Jan. 1976, vol. 15. No. 1,Applied Optics, (4 Pages Total).

* cited by examiner

COMPACT SPECTROMETER SYSTEM FOR NON-INVASIVE MEASUREMENT OF ABSORPTION AND TRANSMISSION SPECTRA IN BIOLOGICAL TISSUE SAMPLES

CROSS-REFERENCE TO RELATED APPLICATIONS

This is a continuation application of U.S. application Ser. No. 15/993,887 filed May 31, 2018, which is a continuation application of U.S. application Ser. No. 15/793,482 (now U.S. Pat. No. 10,004,399), filed on Oct. 25, 2017, which claims priority from Russian Patent Application No. 2016146355, filed on Nov. 25, 2016, in the Russian Federal Service for Intellectual Property, the disclosure of which is incorporated herein in its entirety by reference.

BACKGROUND

Field

Exemplary embodiments relate to optical measurements and optical spectroscopy, particularly for use in medical devices and wearable medical appliances to analyze spectral dependencies of scattering and absorption of optical signals from soft biological tissues of a human, such as skin, blood, biological fluids, etc.

Description of the Related Art

Various methods of non-invasive (e.g., nondestructive) diagnosis of physical and biomedical characteristics of soft tissues are widely used. An optical spectroscopy method is one of the most versatile and informative methods of the non-invasive diagnosis.

Human biological tissues, such as skin, blood, mucous membranes of organs, etc., are known as optically inhomogeneous media for optical radiation. Furthermore, human soft tissues are filled with a variety of light-absorbing biochemical substances, such as water, blood, hemoglobin, etc. Therefore, when the tissues are illuminated with optical radiation, a portion of radiation, having passed in the tissue, experiences multiple re-reflections due to irregularities of the anatomical and cellular structure of the tissue. At the same time, the optical radiation is absorbed by biochemical substances included in the soft tissue. Upon multiple re-reflections and absorption within the tissue, a generally small portion of radiation is emitted toward an outside. This portion of radiation can be detected by an optical receiver.

Various biological (or biochemical) substances of the human body exhibit a pronounced dependence of the absorption coefficient of optical radiation from its spectral content, and this dependence is referred to as "absorption spectrum" which is an individual characteristic of the substance. Irradiation of a biological tissue with an optical radiation having a predetermined power and spectral content, and further analysis of changes in the power and spectral content of the radiation returned from the tissue can provide information about absorption and transmission spectra of the substances contained in the biological tissue. Also, upon further processing by using algorithms, information about current concentration of various light-absorbing biochemical substances in the biological tissue can be obtained.

Most of existing devices for analysis of spectral content of the radiation transmitted through a substance are stationary systems having substantial dimensions and weight. However, modern trends in development of medical equipment require designing personal and portable devices for treatment and diagnosis of various diseases and/or for continuous ongoing monitoring of physical and biomedical condition independently, without involvement of medical personnel.

Therefore, it is desirable that the dimensions and weight of the device are such that the device is portable and can be easily carried by a user. Furthermore, for continuous monitoring of physical and biomedical condition, it is desirable that the device is in constant contact with the soft biological tissue of the person and performs continuous irradiation of this tissue and analysis of the obtained results. For example, the biological tissue to be in contact with the device is human skin (e.g., in the regions of a predetermined thickness or greater, such as skin on the wrist, earlobe, etc.).

SUMMARY

One or more exemplary embodiments provide a compact non-invasive spectrometer system, which provides continuous absorption and/or transmission spectra of an examined biological tissue sample.

One or more exemplary embodiments also provide a compact non-invasive spectrometer system having a desirable size and power consumption, which enables a simpler, more reliable and compact spectrometer system.

One or more exemplary embodiments also provide a compact non-invasive spectrometer system designed for reconstruction of absorption and transmission spectra of an examined biological tissue sample of a human.

One or more exemplary embodiments also provide a compact non-invasive spectrometer system implemented using hardware and software components in combination with a plurality of light-emitting diode sources having broad spectral characteristics, wherein a plurality of special spectral filters are used to obtain for each LED source a plurality of spectral curves having a narrow spectral range and slightly shifted relative to each other, and reconstruction of absorption and/or transmission spectra of the examined sample is attained through algorithmic processing of obtained signals.

According to an aspect of an exemplary embodiment, there is provided a spectrometer including: an illuminating section configured to generate radiation having a spectral content; a receiving section configured to detect the radiation reflected from an object including an optically inhomogeneous scattering medium, the receiving section including at least one optical radiation receiver having a predetermined spectral sensitivity; a hardware section configured to record the radiation, and obtain a solution of an inverse problem to reconstruct an absorption spectrum of the optically inhomogeneous scattering medium included in the object, wherein the illuminating section includes at least one light-emitting diode source, a radiation spectral curve of which is divided, by at least two spectral filters having different spectral transmission curves, into at least two spectral regions, to form an equivalent radiation spectrum from at least two spectral sources, and wherein the hardware section is configured to apply the solution of the inverse problem based on information about the spectral content of the radiation of the illuminating section, a signal obtained in a form of a response from the optically inhomogeneous scattering medium, and a spectral sensitivity curve of the receiving section.

The illuminating section may further include a plurality of infrared light-emitting diode sources.

The illuminating section may further include a redirecting optical system configured to redirect the radiation from the at least one light-emitting diode source to an area of the object being examined.

The illuminating section may further include one or more optical elements for each light-emitting diode source, the one or more optical elements configured to perform an additional collimation of the radiation.

The illuminating section may further include at least one spectral filter for each light-emitting diode source, disposed downstream of the at least one light-emitting diode source.

The receiving section may include an additional optical system configured to redirect the radiation reflected from the object to the at least one optical radiation receiver.

The receiving section may further include at least one spectral filter disposed upstream of the at least one optical radiation receiver.

The illuminating section may further include the at least two spectral filters including a first spectral filter and a second spectral filter, and configured to obtain a spectral curve of the first spectral filter, a peak of which belongs to a lower boundary of a working spectral range of the optically inhomogeneous scattering medium, wherein a spectral curve of the second spectral filter is shifted relative to the spectral curve of the first spectral filter to partially overlap with the spectral curve of the first spectral filter.

According to an aspect of another exemplary embodiment, there is provided a spectrometer including: an illuminating section configured to generate radiation having a spectral content; a receiving section configured to detect the radiation reflected from an object including an optically inhomogeneous scattering medium, the receiving section including at least one optical radiation receiver having a predetermined spectral sensitivity; a hardware section configured to record the radiation, and obtain a solution of an inverse problem to reconstruct an absorption spectrum of the optically inhomogeneous scattering medium included in the object, wherein the illuminating section includes at least one light-emitting diode source, a radiation spectral curve of which is divided, by at least two spectral filters having different spectral transmission curves, into at least two spectral regions, to form an equivalent radiation spectrum from at least two spectral sources, wherein the hardware section is configured to apply the solution of the inverse problem based on information about the spectral content of the illuminating section, a signal obtained in a form of a response from the optically inhomogeneous scattering medium, and a spectral sensitivity curve of the receiving section, and wherein the spectrometer further includes a reference section configured to provide direct measurement of power of the radiation from the illuminating section and automatic calibration of the receiving section.

The illuminating section may further include a plurality of infrared light-emitting diode sources.

The illuminating section may further include a redirecting optical system configured to redirect the radiation from the at least one light-emitting diode source to an area of the object being examined.

The illuminating section may further include one or more optical elements for each light-emitting diode source, the one or more optical elements configured to perform an additional collimation of the radiation.

The illuminating section may further include at least one spectral filter for each light-emitting diode source, disposed downstream of the at least one light-emitting diode source.

The receiving section may include an additional optical system configured to redirect the radiation reflected from the object to the at least one optical radiation receiver.

The receiving section may further include at least one spectral filter disposed upstream of the at least one optical radiation receiver.

The illuminating section may further include the at least two spectral filters including a first spectral filter and a second spectral filter, and configured to obtain a spectral curve of the first spectral filter, a peak of which belongs to a lower boundary of a working spectral range of the optically inhomogeneous scattering medium, wherein a spectral curve of the second spectral filter is shifted relative to the spectral curve of the first spectral filter to partially overlap with the spectral curve of the first spectral filter.

According to an aspect of still another exemplary embodiment, there is provided a spectrometer including: an illuminating section including at least one light-emitting diode source, each configured to emit radiation having a spectral content; a radiation receiver configured to detect the radiation reflected from an object including an optically inhomogeneous scattering medium, the radiation receiver including at least one optical radiation receiver having a predetermined spectral sensitivity; a processor configured to solve an inverse problem to reconstruct an absorption spectrum of the optically inhomogeneous scattering medium included in the object, based on information about the spectral content of the radiation emitted by the at least one light-emitting diode source, a signal obtained in a form of a response from the optically inhomogeneous scattering medium, and a spectral sensitivity curve of the radiation receiver.

The illuminating section may further include at least two spectral filters configured to divide a radiation spectral curve of the at least one light-emitting diode source into at least two spectral regions.

The at least two spectral filters may include a first spectral filter and a second spectral filter and a spectral curve of the second spectral filter may be shifted relative to a spectral curve of the first spectral filter to partially overlap with the spectral curve of the first spectral filter.

According to an aspect of another exemplary embodiment, there is provided a spectrometer including: at least one light-emitting diode source configured to emit radiation having a spectral characteristic to an optically inhomogeneous scattering medium; a radiation receiver configured to detect a scattered radiation from the optically inhomogeneous scattering medium; a processor configured to reconstruct an absorption spectrum of the optically inhomogeneous scattering medium, based on information about the spectral characteristic of the radiation emitted by the at least one light-emitting diode source, and a signal obtained from the radiation receiver in response to detection of the scattered radiation.

The processor may be further configured to reconstruct the absorption spectrum based on a result of calibration of at least one of the spectral characteristic and the signal obtained from the radiation receiver.

The result of calibration may include at least one of a result of calibration of the spectral characteristic based on a first temperature of the at least one light-emitting diode source or a result of calibration of the signal obtained from the radiation receiver based on a second temperature of the radiation receiver.

The spectrometer may further include a first temperature detector configured to obtain the first temperature of the at least one light-emitting diode source; and/or a second temperature detector configured to obtain the second temperature of the radiation receiver.

The result of calibration may further include a result of calibration of the spectral characteristic based on a first temperature of the at least one light-emitting diode source and a current flow through the at least one light-emitting diode source.

The processor may be further configured to reconstruct the absorption spectrum by solving an inverse problem based on the information about the spectral characteristic and the signal obtained from the radiation receiver.

The spectrometer may further include a reference section configured to detect power of the radiation emitted by the at least one light-emitting diode source.

The reference section may include a light detector that is disposed in proximity of the at least one light-emitting diode source, the light detector being configured to detect the radiation emitted by the at least one light-emitting diode source.

The processor may be further configured to estimate a spectrum error based on the reconstructed absorption spectrum and data from the light detector, and to determine whether the spectrum error is less than a threshold.

The processor may be further configured to output the reconstructed absorption spectrum based on a result of determining that the spectrum error is less than the threshold.

The processor may be further configured to, based on a result of determining that the spectrum error is not less than the threshold, perform calibration on the signal obtained from the radiation receiver and reconstruct the absorption spectrum based on the spectral characteristic and the calibrated signal obtained from the radiation receiver.

The processor may be further configured to reconstruct the absorption spectrum based on the information about the spectral characteristic and the calibrated signal obtained from the radiation receiver until it is determined that the spectrum error is less than the threshold.

The at least one light-emitting diode source may include a plurality of light-emitting diodes that have powers and pulse durations that are different from each other.

The processor may be further configured to reconstruct the absorption spectrum of the optically inhomogeneous scattering medium, based on information about a plurality of spectral characteristics of radiations emitted by the plurality of light-emitting diodes, and signals obtained from the radiation receiver in response to detection of scattered radiations from the optically inhomogeneous scattering medium.

The processor may be further configured to obtain the plurality of spectral characteristics of the radiations emitted by the plurality of light-emitting diodes and the signals obtained from the radiation receiver, by successively switching the plurality of light-emitting diodes.

The processor may be further configured to perform calibration on a spectral characteristic of a given light-emitting diode source among the plurality of light-emitting diodes according to a first temperature of the given light-emitting diode source.

BRIEF DESCRIPTION OF THE DRAWINGS

The above and/or other aspects will be more apparent by describing certain exemplary embodiments with reference to the accompanying drawings, in which.

DETAILED DESCRIPTION

Figure 1:
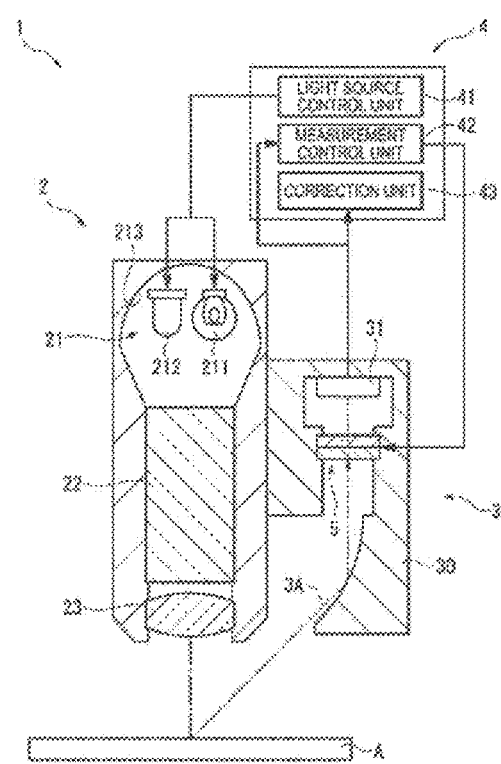
FIG. 1 shows a spectrometer system based on a spectral element that divides radiation according to a spectral range.

As the inventive concept allows for various changes and numerous exemplary embodiments, particular exemplary embodiments will be illustrated in the drawings and described in detail in the written description. However, this is not intended to limit the disclosure to particular modes of practice, and it is to be appreciated that all modifications, equivalents, and/or alternatives that do not depart from the spirit and technical scope of the disclosure are encompassed in the inventive concept. In the description, certain detailed explanations of the related art are omitted when it is deemed that they may unnecessarily obscure the essence of the disclosure.

Figure 2:
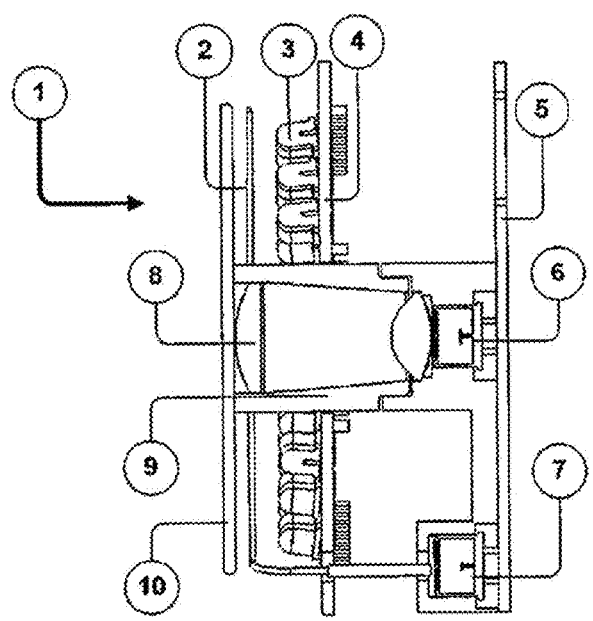
FIG. 2 shows a spectrometer system based on a plurality of light-emitting diodes (LEDs)

FIG. 1 shows a spectrometer system based on a spectral element that divides radiation according to a spectral range. FIG. 2 shows a spectrometer system based on a plurality of light-emitting diodes (LEDs).

The spectrometer systems shown in FIGS. 1 and 2 are based on the principle of determining the composition of an inhomogeneous absorbing optical medium based on the analysis of changes in the spectral content of the radiation transmitted through the optical medium.

The spectrometer system shown in FIG. 1 is a related art optical spectrometer based on a tungsten lamp (e.g., incandescent lamp with a tungsten filament), as disclosed in U.S. patent application No. 2014/0168636, and includes at least one radiation source on the basis of a tungsten lamp with a broad spectral range, guiding and collimating optics for guiding light towards a test target, as well as a receiving channel with an optical system, a light detector, and an element for dividing the light by a spectrum in the form of a Fabry-Perot cavity.

As illustrated in FIG. 1, a spectrometer 1 includes a light source device 2 which emits light toward a test target A, a dividing device 3 which has an etalon 5 (e.g., wavelength variable range: 380 nm to 780 nm) for dividing test target light reflected by the test target A, and a control device 4 which controls the overall operation of the spectrometer 1. The light source device 2 includes a light source unit 21, a light mixer 22, and a lens 23 as components combined into one body. The light source unit 21 has a tungsten lamp 211 emitting white light, the violet LED 212, and a reflector 213 which reflects light emitted from the tungsten lamp 211 and the violet LED 212. The dividing device 3 includes a device main body 30 which has a concave mirror 3A for reflecting the test target light reflected by the test target A such that the test target light can travel in a predetermined direction and converge on the etalon 5. The device main body 30 has the etalon 5 (wavelength variable interference filter) which divides test target light received from the concave mirror 3A, and a light receiving unit 31 which receives light having respective wavelengths after division by the etalon 5. The control device 4 includes a light source control unit 41, a measurement control unit 42, and a correction unit 43.

The spectrometer provides a rather high spectral resolution, but at the same time it has several disadvantages, in particular:

1. use of a tungsten lamp dictates a quite large size of the device, which is unsuitable for a wearable device;

2. Fabry-Perot cavity used as a spectrum-selective element has an extremely low efficiency. Due to the low efficiency, this structure requires high power of input light emitted by the tungsten lamp, which poses additional requirements for the size of the device and its power supply, thereby making compact design almost infeasible; and 3. also, the use of Fabry-Perot cavity poses substantial restrictions on the spectral resolution of the device and causes manifold complexity in tuning up the device, thereby complicating its assembly and subsequent refinement in service.

A spectrometer 1 shown in FIG. 2 is another related art optical spectrometer based on the use of light emitting diodes (LEDs) as optical radiation sources, as disclosed in International Publication No. WO 2010/082852, and includes a plurality of LEDs 3, LED controller electronics 4, a reference fibre 2 to deflect a portion of radiation to a reference light detector 7, detector electronics 5, a detector optics 8 and a main light detector 6. Also shown are a detector optics mounting device 9, and a window to allow light in and out 10. Spectral resolution is here provided by the great number of LEDs, each emitting radiation of own spectral range, and the total efficiency of the system is achieved by switching on the LEDs individually in a specified sequence, followed by processing the obtained signal. It should be noted that the use of a finite number of LEDs prevents obtaining a continuous absorption and/or transmission spectrum of the examined sample.

With this structure of the spectrometer optics, each LED source provides only a single point on the measured absorption curve of the sample. This means that the entire measured absorption curve will have a resolution equal to the width of the spectral range in which the measurements are made, divided by the number of LEDs being used.

Disadvantages of the related art systems, as stated above, include the fact that there is only one way to improve the spectral resolution, particularly, by increasing the number of LED sources, which leads to increasing not only the size of the device, but also its power consumption. The increased power consumption makes a compact portable design infeasible.

Figure 3:
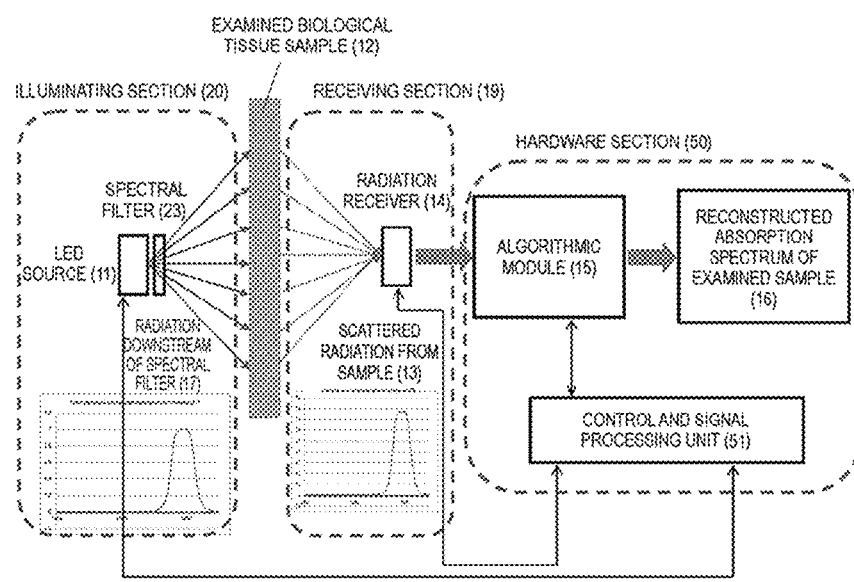
FIG. 3 illustrates an operation of a spectrometer system according to an exemplary embodiment.

FIG. 3 schematically illustrates an operation of a compact non-invasive spectrometer according to an exemplary embodiment. Radiation from one or more light-emitting diode (LED) sources 11 included in an illuminating section 20 passes through two or more spectral filters 23 and irradiates a sample 12 including a soft biological tissue. Upon multiple re-reflections and partial absorption in the optically inhomogeneous biological tissue, the radiation is emitted from the examined sample 12 in the form of scattered radiation 13. Spectral content of the scattered radiation 13 differs from that of radiation passed through the spectral filter 17 due to different absorption for various spectral components in the examined sample 12. The scattered radiation 13 is received by a radiation receiver 14, which is included in a receiving section 19 and detects the radiation 13. The signal received from the radiation receiver 14 enters an algorithmic module 15 included in a hardware section 50. The algorithmic module 15 also receives data about the spectral content of the radiation downstream of the spectral filter 17. Then, by mathematical processing of the signal to represent the signal in the normalized form and by solution of the inverse problem, the algorithmic module 15 reconstructs the absorption spectrum of the examined sample 16. A control and signal processing unit 51 performs monitoring and control of the LED sources 11, the radiation receiver 14 and the algorithmic module 15. The hardware section 50 including the algorithmic module 15 and the control and signal processing unit 51 may be implemented and executed by a hardware processor such as a microprocessor.

Figure 4:
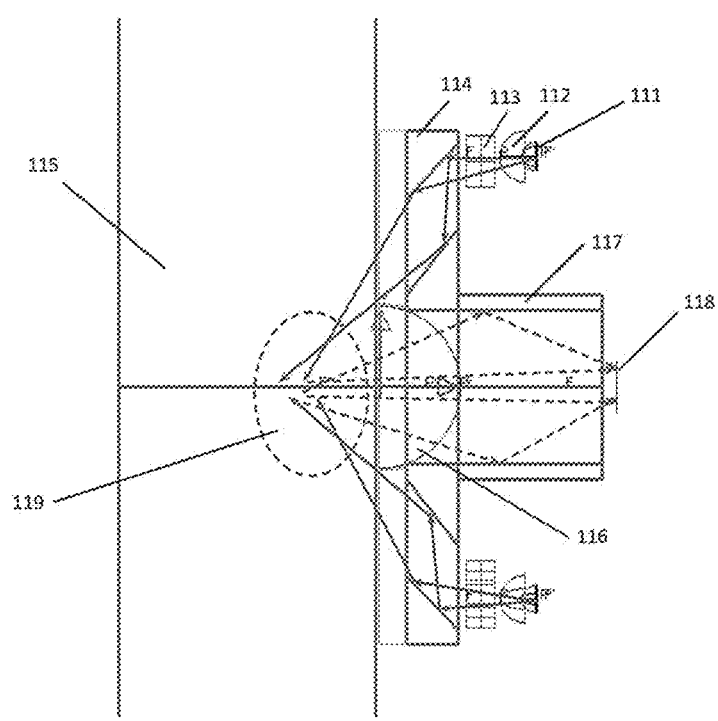
FIG. 4 shows an optical scheme, including illuminating and receiving sections, of a spectrometer according to an exemplary embodiment.

FIG. 4 shows an optical scheme, including illuminating and receiving sections, of a spectrometer according to an exemplary embodiment.

The compact spectrometer system according to an exemplary embodiment combines an optical system and software in a hardware and software components and includes:

an illuminating section, which generates radiation having a predetermined spectral content varying responsive to a control signal, and includes at least one LED source and at least two spectral filters;

a receiving section, which detects optical radiation returned from the analyzed optically inhomogeneous, bulk scattering medium, and includes at least one optical radiation receiver with a known spectral sensitivity;

a hardware section including a signal processing and control unit and an algorithmic module, which provide solution of the inverse problem for reconstruction of the absorption spectrum of the examined optically inhomogeneous medium.

The exemplary embodiments may be implemented by combining, in the spectrometer system, the algorithmic module containing software and optical and mechanical equipment.

The illuminating section, which is included in the spectrometer system according to an exemplary embodiment, enables forming a regular, evenly illuminated area with predetermined dimensions at a specified point of the sample to be examined.

The receiving section of the spectrometer system is designed for detecting optical radiation from the illuminating section returned after passing through the examined sample. An exemplar embodiment of the illuminating and receiving sections, as well as their arrangement and interaction are shown in FIG. 4.

Referring to FIG. 4, radiation from LED sources 111 passes through an optical element intended for additional collimation of the radiation and having the form of a lens element 112, then through a spectral filter 113, which performs an additional conversion of spectral characteristic of the transmitted radiation into a desirable form, in particular, changes the shape and shifts the central peak of the spectral characteristic. Then the radiation enters a redirecting optical system including a redirecting element 114 including a reflective material, and a conical part of a converging cylinder 117, which altogether form an air light guide changing the radiation direction so as to provide uniform illumination of a desired region of a sample 115 to be examined. At entrance to the sample 115, the radiation is partially reflected from the sample/air interface and partially passes into the sample 115. The radiation reflected from the sample/air interface is effectively removed from the optical path of the spectrometer by using the special structure of the receiving section, a first element of which is a thick-wall cylinder that prevents the radiation scattered at the sample/air interface to enter the receiving section. The radiation entered the bulk of the sample 115 to an examined area 119 undergoes multiple re-reflections from structural heterogeneities of the sample 115 and, as a result of the re-reflections, is partially emitted from the sample 115 in the opposite direction. Having emitted in the opposite direction, the radiation enters the receiving section of the spectrometer according to an exemplary embodiment. Here the radiation passes through an additional optical system designed to redirect the optical radiation and including a collimating lens 116 and a converging cylinder 117 including a reflective material, and then enters a radiation receiver 118 provided in the form of a sole light detector.

Figure 5:
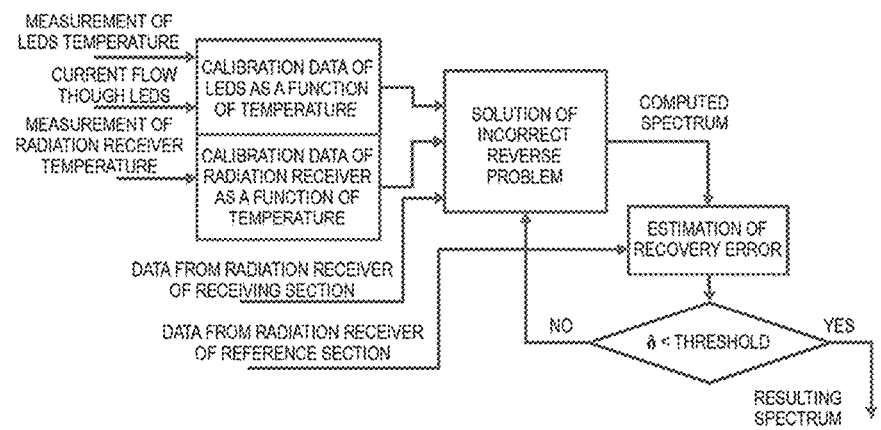
FIG. 5 shows a schematic diagram of an algorithmic module of a spectrometer according to an exemplary embodiment.

FIG. 5 shows a schematic diagram of processing the obtained signals in the algorithmic module according to an exemplary embodiment.

In an exemplary embodiment, LED sources operate in a pulsed mode. Therefore, as shown above, using different pulse duration and power, as well as successively switching on a plurality of LED sources with a plurality of spectral filters, a set of linearly independent data on a spectral response of the examined sample can be acquired. The data forms a system of linearly independent equations. Also, to increase the number of linearly-independent equations, a plurality of detectors can be used with additional optical filters having different values of spectral transmission peaks. All these measures enable increasing the number of linearly independent equations and accordingly improve the accuracy of reconstruction of absorption and transmission spectra.

A reconstructed spectrum can be obtained by solving the system of linear equation in a matrix form, as expressed in equation (1):

$$Az=u,$$

where A is the matrix of coefficients determined by spectral characteristics of the LEDs; u is the matrix of free terms—data measured on the light detector; z is the spectrum to be reconstructed.

In this problem, matrix A may be ill-conditioned. Therefore, solution of the system of linear equation (1) may be incorrect. One of the most accurate and sustainable methods of its solution is the Tikhonov's method of regularization.

The Tikhonov's method of regularization involves introduction of regularizing parameter $\alpha$, where $\alpha>0$. Equation (2) is expressed as:

$$(\alpha E + A^T A)z_\alpha = A^T u, \qquad (2),$$

where E is an identity matrix.

System of linear equation (2) can be solved by any known method, for example, by the method of least squares. In an exemplary embodiment, QR decomposition may be used.

Since spectral characteristics of LEDs and light detectors are affected by their temperature, to improve the accuracy of reconstruction of absorption and transmission spectra, data on current temperature of LED sources and light detectors can be used. The temperature data can be taken into account when matrix A is set.

Figure 6:
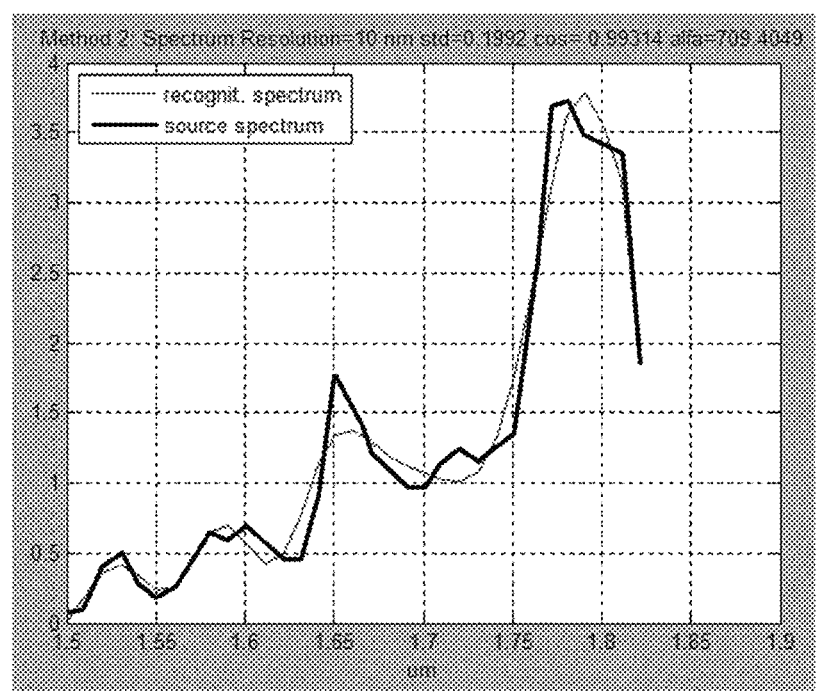
FIG. 6 shows an example of a reconstructed spectrum of a sample examined by a spectrometer according to an exemplary embodiment.

Solution of system of linear equation (2) provides the reconstructed absorption or transmission spectrum of the examined sample. The reconstructed spectrum is continuous depending on the wavelength. An example of the reconstructed absorption spectrum and its comparison with the original absorption spectrum of the examined sample is shown in FIG. 6.

Figure 9:
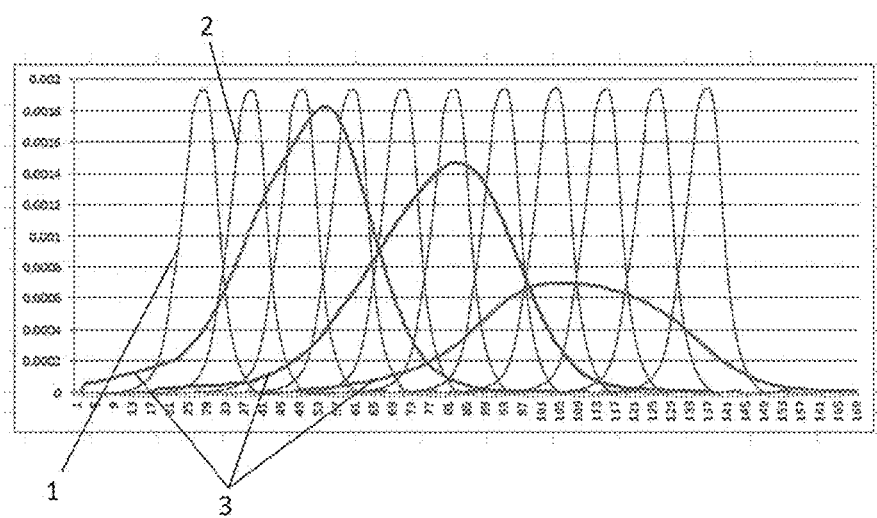
FIG. 9 shows exemplary curves of spectral filters in combination with spectral characteristics of LED sources according to an exemplary embodiment.

The set of LED sources and spectral filters, used in an exemplary embodiment, allows obtaining individual spectral curves shifted relative to each other in the following manner, as shown in FIG. 9. Referring to FIG. 9, a spectral curve of the first spectral filter 1 is selected so that its peak falls on the lower boundary of the examined spectral range, and the width of the spectral curve is sufficient to partially overlap the spectral curve of the following spectral filter 2. A spectral curve of each subsequent spectral filter is shifted relative to the previous curve such that spectral curve peaks are shifted relative to each other, and the spectral curves, as such, partially overlap with each other based on the sufficient width thereof. Since spectral characteristics 3 of the LED sources are wide enough, a set of a plurality of spectral filters for a single LED source enables obtaining a set of continuously shifted spectral curves. On the boundary of spectral characteristics of two LED sources, spectral curves of the filters are chosen so as to ensure continuous shifting of spectral curves. Additionally, the electronic path of the inventive compact non-invasive spectrometer system is designed such that the pulse length and the radiation power of the LED sources can be varied. It also allows further shifting of spectral characteristics of LED sources due to their heating or cooling.

With this choice of the set of spectral characteristics of LED sources, spectral curves of the filters and the electronic path of the spectrometer, the totality of spectral characteristics of LED sources is used for subsequent reconstruction of the absorption spectrum of the examined sample. In this case, not the direct problem of measuring the absorption spectrum is solved, as in the described related art systems, but the inverse problem of reconstructing the absorption spectrum from known spectral responses from the examined sample is solved. By using the inverse problem solution, the spectrometer system according to an exemplary embodiment poses no restrictions on the magnitude of spectral resolution and allows reconstruction of spectral absorption curve of the examined sample with high accuracy at a minimum number of used spectral curves and, therefore, a minimum number of LED sources used.

Figure 8:
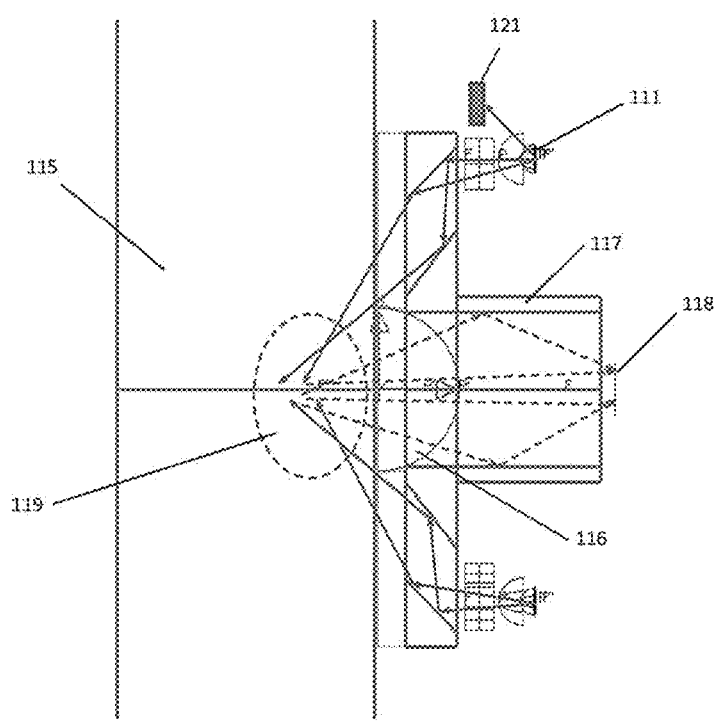
FIG. 8 shows an optical scheme, including illuminating, receiving and reference sections, of a spectrometer according to an exemplary embodiment.

In addition, to improve the accuracy of reconstruction of absorption spectrum of the examined sample and to account for possible processes of degradation of LED sources, a compact non-invasive spectrometer according to an exemplary embodiment may be supplemented with a reference section 121, as shown in FIG. 8. The reference section 121, in an exemplary embodiment, includes a single light detector disposed in an immediate vicinity of the LED sources, which is intended for direct measurement of the integral power of the radiation emitted by the LED sources.

Figure 7:
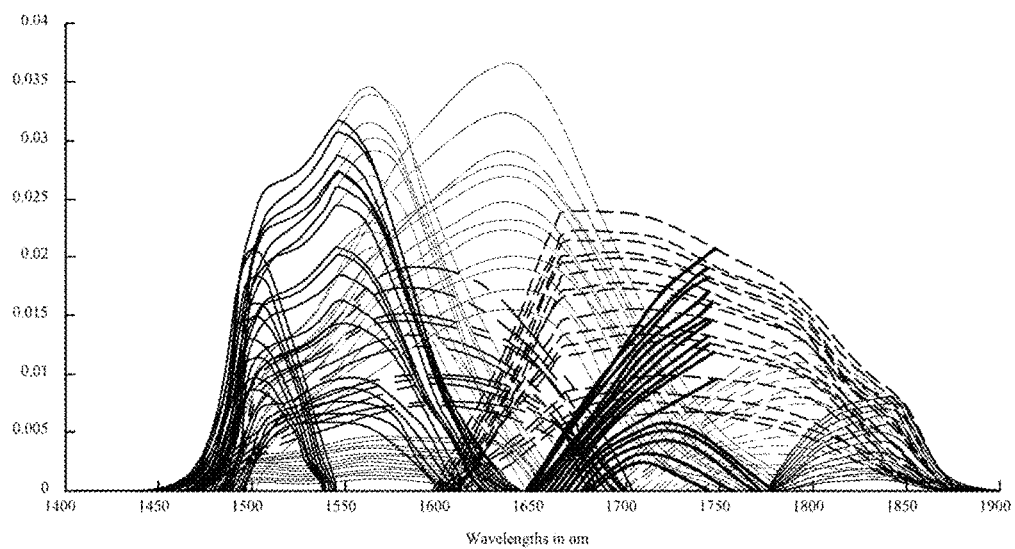
FIG. 7 shows an example of spectral characteristics of LED sources at different modes of radiation pulse duration and power according to an exemplary embodiment.

To enhance the accuracy of reconstruction of absorption spectrum of the examined sample, it is desirable to increase the number of independent measurements for each sample being examined. One of the simplest methods to achieve this is to control the power and pulse duration of the LED sources. Spectral content of radiation of LED sources is known to be dependent on the duration of the radiated pulse (e.g., in a pulsed operation mode of LED source) and the magnitude of control signal (e.g., current or voltage), which is proportional to the power of the LED source. Therefore, according to the control by the signal processing and control unit with respect to the duration and power of pulse of the LED source, spectral characteristics of the LED source may be effectively varied and the number of independent measurements may be increased for a single examined sample and for a single LED source. When there are a plurality of LED sources, the plurality of LED sources are switched on successively, and for each of the plurality of LED sources, measurements are made in multiple states characterized by different pulse duration and different power. FIG. 7 shows typical spectral characteristics of LED sources that can be used in an exemplary embodiment, as well as their dependence on the duration of the radiation pulse and its power.

All signals from the light detector are forwarded to the algorithmic module, which reconstructs absorption and transmission spectra of the examined sample.

Reconstruction or interpretation of the original signal from a known output signal is a classic example of the inverse problem solution. In an exemplary embodiment, the inverse problem solution involves finding the true shape of the absorption spectrum curve of the examined sample from known responses from the sample to a radiation having a priori known spectral content.

According to exemplary embodiments, the technical effect is attained by using hardware and software components of a spectrometer for non-invasive measurement of absorption or transmission spectra of bulk scattering, optically inhomogeneous media, which has a compact design and enables obtaining a continuous absorption and/or transmission spectrum of an examined sample of human soft biological tissues, as well as an embodiment of an optical system of the spectrometer and an algorithmic section for reconstruction of absorption and/or transmission spectra.

At least one of the components, elements, modules or units represented by a block as illustrated in the drawings may be embodied as various numbers of hardware, software and/or firmware structures that execute respective functions described above, according to an exemplary embodiment. For example, at least one of these components, elements or units may use a direct circuit structure, such as a memory, a processor, a logic circuit, a look-up table, etc. that may execute the respective functions through controls of one or more microprocessors or other control apparatuses. Also, at least one of these components, elements or units may be specifically embodied by a module, a program, or a part of code, which contains one or more executable instructions for performing specified logic functions, and executed by one or more microprocessors or other control apparatuses. Also, at least one of these components, elements or units may further include or implemented by a processor such as a central processing unit (CPU) that performs the respective functions, a microprocessor, or the like. Two or more of these components, elements or units may be combined into one single component, element or unit which performs all operations or functions of the combined two or more components, elements of units. Also, at least part of functions of at least one of these components, elements or units may be performed by another of these components, element or units. Further, although a bus is not illustrated in the above block diagrams, communication between the components, elements or units may be performed through the bus. Functional aspects of the above exemplary embodiments may be implemented in algorithms that execute on one or more processors. Furthermore, the components, elements or units represented by a block or processing steps may employ any number of related art techniques for electronics configuration, signal processing and/or control, data processing and the like.

The "unit" or "module" used herein may be a hardware component, such as a processor or a circuit, and/or a software component that is executed by a hardware component such as a processor.

While one or more exemplary embodiments have been described with reference to the figures, it will be understood by those of ordinary skill in the art that various changes in form and details may be made therein without departing from the spirit and scope of the inventive concept as defined by the following claims.

What is claimed is:

1. A spectrometer comprising:
    at least one light-emitting diode source configured to emit radiation having a spectral characteristic to an optically inhomogeneous scattering medium;
    a radiation receiver configured to detect a scattered radiation from the optically inhomogeneous scattering medium;
    a processor configured to reconstruct an absorption spectrum of the optically inhomogeneous scattering medium, based on information about the spectral characteristic of the radiation emitted by the at least one light-emitting diode source, and a signal obtained from the radiation receiver in response to detection of the scattered radiation; and
    a reference section comprising a light detector, the light detector configured to detect the radiation emitted by the at least one light-emitting diode source, the reference section configured to estimate a spectrum error based on the reconstructed absorption spectrum and data from the light detector,
    wherein the light detector is closer in proximity to the at least one light-emitting diode source than the radiation receiver to the at least one light-emitting diode source.

2. The spectrometer of claim 1, wherein the processor is further configured to reconstruct the absorption spectrum based on a result of calibration of at least one of the spectral characteristic and the signal obtained from the radiation receiver.

3. The spectrometer of claim 2, wherein the result of calibration comprises at least one of a result of calibration of the spectral characteristic based on a first temperature of the at least one light-emitting diode source or a result of calibration of the signal obtained from the radiation receiver based on a second temperature of the radiation receiver.

4. The spectrometer of claim 3, further comprising:
    a first temperature detector configured to obtain the first temperature of the at least one light-emitting diode source; and/or
    a second temperature detector configured to obtain the second temperature of the radiation receiver.

5. The spectrometer of claim 2, wherein the result of calibration further comprises a result of calibration of the spectral characteristic based on a first temperature of the at least one light-emitting diode source and a current flow through the at least one light-emitting diode source.

6. The spectrometer of claim 1, wherein the processor is further configured to determine whether the spectrum error is less than a threshold.

7. The spectrometer of claim 6, wherein the processor is further configured to output the reconstructed absorption spectrum based on a result of determining that the spectrum error is less than the threshold.

8. The spectrometer of claim 6, wherein the processor is further configured to, based on a result of determining that the spectrum error is not less than the threshold, perform calibration on the signal obtained from the radiation receiver and reconstruct the absorption spectrum based on the spectral characteristic and the calibrated signal obtained from the radiation receiver.

9. The spectrometer of claim 8, wherein the processor is further configured to reconstruct the absorption spectrum based on the information about the spectral characteristic and the calibrated signal obtained from the radiation receiver until it is determined that the spectrum error is less than the threshold.

10. The spectrometer of claim 1, wherein the at least one light-emitting diode source comprises a plurality of light-emitting diodes that have powers and pulse durations that are different from each other.

11. The spectrometer of claim 10, wherein the processor is further configured to reconstruct the absorption spectrum of the optically inhomogeneous scattering medium, based on information about a plurality of spectral characteristics of radiations emitted by the plurality of light-emitting diodes, and signals obtained from the radiation receiver in response to detection of scattered radiations from the optically inhomogeneous scattering medium.

12. The spectrometer of claim 11, wherein the processor is further configured to obtain the plurality of spectral characteristics of radiations emitted by the plurality of light-emitting diodes and the signals obtained from the radiation receiver, by successively switching the plurality of light-emitting diodes.

13. The spectrometer of claim 12, wherein the processor is further configured to perform calibration on a spectral characteristic of a given light-emitting diode source among the plurality of light-emitting diodes according to a first temperature of the given light-emitting diode source.

14. A spectrometer comprising:
at least one light-emitting diode source configured to emit radiation having a spectral characteristic to an optically inhomogeneous scattering medium;
a radiation receiver configured to detect a scattered radiation from the optically inhomogeneous scattering medium; and
a processor configured to reconstruct an absorption spectrum of the optically inhomogeneous scattering medium, based on information about the spectral characteristic of the radiation emitted by the at least one light-emitting diode source, and a signal obtained from the radiation receiver in response to detection of the scattered radiation,
wherein the processor is further configured to reconstruct the absorption spectrum by performing calibration based on a temperature of the at least one light-emitting diode source and a current flow through the at least one light-emitting diode source.

15. A spectrometer comprising:
at least one light-emitting diode source configured to emit radiation having a spectral characteristic to an optically inhomogeneous scattering medium;
a radiation receiver configured to detect a scattered radiation from the optically inhomogeneous scattering medium; and
a processor configured to solve an inverse problem of reconstructing an absorption spectrum of the optically inhomogeneous scattering medium, based on information about the spectral characteristic of the radiation, and a signal obtained from the radiation receiver in response to detection of the scattered radiation, and further based on at least one of a first temperature of the at least one light-emitting diode source or a second temperature of the radiation receiver.

* * * * *